(12) United States Patent
Song et al.

(10) Patent No.: US 12,104,435 B2
(45) Date of Patent: Oct. 1, 2024

(54) NON-CONTACT SAFETY RELAYING APPARATUS FOR TRANSFERRING OBJECT

(71) Applicant: Jong Woon Song, Gwangju (KR)

(72) Inventors: Jong Woon Song, Gwangju (KR); Kwang Choon Ji, Gwangju (KR)

( * ) Notice: Subject to any disclaimer, the term of this patent is extended or adjusted under 35 U.S.C. 154(b) by 770 days.

(21) Appl. No.: 17/418,051

(22) PCT Filed: Apr. 23, 2021

(86) PCT No.: PCT/KR2021/005209
§ 371 (c)(1),
(2) Date: Jun. 24, 2021

(87) PCT Pub. No.: WO2021/251618
PCT Pub. Date: Dec. 16, 2021

(65) Prior Publication Data
US 2022/0333436 A1 Oct. 20, 2022

(30) Foreign Application Priority Data
Jun. 11, 2020 (KR) .......................... 10-2020-0070619

(51) Int. Cl.
*E06B 7/32* (2006.01)
*A61B 50/30* (2016.01)
(Continued)

(52) U.S. Cl.
CPC ................ *E06B 7/32* (2013.01); *A61B 50/30* (2016.02); *A61L 2/22* (2013.01); *A61L 2/24* (2013.01);
(Continued)

(58) Field of Classification Search
CPC ... E06B 7/32; A61B 50/30; A61L 2/22; A61L 2/24; A61L 2202/121; A61L 2202/122; A61L 2202/14
(Continued)

(56) References Cited

U.S. PATENT DOCUMENTS 1,407,965 A * 2/1922 Ware .......................... C11B 1/04
220/502
2,515,137 A * 7/1950 Schall .................. A23B 7/0053
126/369
(Continued)

FOREIGN PATENT DOCUMENTS

KR 10-2017-0133088 A 12/2017
KR 102150224 B1 * 8/2020

*Primary Examiner* — J. Gregory Pickett
*Assistant Examiner* — Niki M Eloshway
(74) *Attorney, Agent, or Firm* — Brooks, Cameron & Huebsch, PLLC (57) ABSTRACT

Proposed is a non-contact safety relaying apparatus for transferring an object, the apparatus including: an apparatus body including, a main body formed to have an internal space through which first and second independent spaces communicate, a horizontal partition extending horizontally at a height of a center of the main body, with at least one relaying hole being pierced therethrough, an upper partition extending upward from a first side of the horizontal partition and forming a first relaying space, a lower partition extending downward from a second side thereof and forming a second relaying space, a first door mounted on the main body in such a manner as to open and close the first relaying space, and a second door mounted on the main body in such a manner as to open and close the second relaying space; and an opening and closing unit opening and closing the relaying hole.

6 Claims, 8 Drawing Sheets

(51) Int. Cl.
*A61L 2/22* (2006.01)
*A61L 2/24* (2006.01)

(52) U.S. Cl.
CPC ... *A61L 2202/121* (2013.01); *A61L 2202/122* (2013.01); *A61L 2202/14* (2013.01); *A61L 2202/15* (2013.01); *A61L 2202/24* (2013.01)

(58) Field of Classification Search
USPC ............................................ 220/4.01, 5.1, 5.2
See application file for complete search history.

(56) References Cited

U.S. PATENT DOCUMENTS

| | | | | |
|---|---|---|---|---|
| 6,027,392 | A * | 2/2000 | Ruhlman | A63H 33/00 220/502 |
| 8,006,859 | B2 * | 8/2011 | Clarke | A47F 1/04 220/500 |
| 2008/0283424 | A1 * | 11/2008 | Palamara | B65D 81/3222 206/229 |
| 2012/0055935 | A1 * | 3/2012 | Peres | B65D 81/3211 220/502 |
| 2014/0217102 | A1 * | 8/2014 | Wilson | B65D 5/443 220/501 |
| 2014/0328633 | A1 * | 11/2014 | Nierescher | B65F 5/005 406/154 |
| 2019/0365939 | A1 * | 12/2019 | Mcginnis | A23L 3/3445 |

* cited by examiner

NON-CONTACT SAFETY RELAYING APPARATUS FOR TRANSFERRING OBJECT

TECHNICAL FIELD

The present invention relates to a non-contact safety relaying apparatus for transferring an object and, more particularly, to a non-contact safety relaying apparatus for transferring an object, the apparatus being capable of safely transferring the object in a non-contact manner.

BACKGROUND ART

Generally, the initial symptoms of an infected person are not serious and an infected person can walk around without much difficulty. For this reason, the infected person may walk around without any restriction within a hospital. However, the infected person may infect other people in the hospital or may infect a diagnostician while being diagnosed.

Particularly, in the case of unexpected infectious diseases, such as recently-occurring Middle East Respiratory Syndromes (MERS) and COVID-19, there occurs a problem in that these infectious diseases are rapidly spread in the medical field of diagnosis of infectious diseases.

In order to solve these problems, a booth for obtaining a specimen in sputum or in a mucous membrane of a respiratory organ and preventing spread of infection to the outside while obtaining the specimen, in a separation space in which an infected patient or a person suspected of being infected can be separated, was disclosed in Korean Patent Application Publication No. 10-2017-0133088.

However, with a method of obtaining the specimen using this booth, the time for obtaining the specimen cannot be shortened. Thus, there is a need for a structure where the specimen is obtained while a negative pressure is maintained in an independent specimen obtaining space which is large enough to accommodate a person obtaining the specimen and where a kit containing the specimen (hereinafter, a specimen containing kit) is safely transferred to a collection chamber in which a positive pressure is maintained and is separated from the specimen obtaining space.

DISCLOSURE

Technical Problem

An objective of the present invention, which is made in view of solving the above-described problems, is to provide a non-contact safety relaying apparatus for transferring an object, which is capable of safely transferring the object in a non-contact manner between different partition spaces while preventing spread of infection.

Technical Solution

In order to achieve the above-described objective, according to an aspect of the present invention, there is provided a non-contact safety relaying apparatus for transferring an object, which is arranged between a first independent space and a second independent space separated independently of each other and is configured to relay the object introduced into the first independent space in such a manner as to be stably transferred into the second independent space in a non-contact manner, the apparatus including: an apparatus body including, a main body being formed to have an internal space through which the first independent space and the second independent space communicate with each other and being arranged in a direction that traverses the first independent space and the second independent space, a horizontal partition extending horizontally at a height of a center of the main body, with at least one relaying hole being formed to be pierced through the horizontal partition, an upper partition extending upward from a first side of the horizontal partition and forming a first relaying space exposed to the first independent space, a lower partition extending downward from a second side which is the opposite side of the horizontal partition and forming a second relaying space exposed to the second independent space, a first door mounted on the main body in such a manner as to open and close the first relaying space, and a second door mounted on the main body in such a manner as to open and close the second relaying space; and an opening and closing unit configured to open and close the relaying hole in the horizontal partition.

In the non-contact safety relaying apparatus, the opening and closing unit may include: a slider being arranged under the horizontal partition and being configured to open and close the relaying hole by a sliding movement thereof, with a communicating hole being formed in the slider to communicate with the relaying hole; a guide portion being positioned under the slider and being combined with the apparatus body in a manner that is supportable on the apparatus body, with a rail being formed on an upper portion of the guide portion; and a movable insertion piece being combined with a bottom portion of the slider and being moved in a secured state along the rail.

In the non-contact safety relaying apparatus, the opening and closing unit may include: an upright-positioned cylindrical pipe having an internal hole vertically pierced therethrough and extending downward from a bottom portion of the horizontal partition in such a manner as to communicate with the relaying hole in the horizontal partition; an upper opening and closing plate being mounted into an upper inlet-outlet hole in a manner that is movable backward and forward, in such a manner as to pass through the upper inlet-outlet hole formed in the upright-positioned cylindrical pipe and to move horizontally within the upright-positioned cylindrical pipe, thereby closing and opening the internal hole, a lower opening and closing plate being mounted into a lower inlet-outlet hole in a manner that is movable backward and forward, in such a manner as to pass through the lower inlet-outlet hole formed at a distance below the upper inlet-outlet hole and to move horizontally within the upright-positioned cylindrical pipe, thereby closing and opening the internal hole, a first load cell mounted on the upper opening and closing plate; a second load cell mounted on the lower opening and closing plate; a first actuator moving the upper opening and closing plate backward and forward; a second actuator moving the lower opening and closing plate backward and forward; and a controller configured to determine that a standby mode is entered, when signals detected by the first load cell and the second load cell indicate a non-load state, control in the standby mode the first and second actuators in such a manner that both the upper opening and closing plate and the lower opening and closing plate are loaded at positions, respectively, for closing the internal hole, control the first actuator in such a manner that the upper opening and closing plate is moved to a position for opening the internal hole, after a preset first elapse time, when a load detection signal indicating safe arrival of the object is received from the first load cell in the standby mode, control the first actuator in such a manner that the upper opening and closing plate is moved to the position for closing the internal hole and control the second actuator in such a manner that the lower opening and closing plate is moved to a position for opening the internal hole and thus the object drops, when a load detection signal indicating safe arrival of the dropping object is received from the second load cell, and control the second actuator in such a manner that the lower opening and closing plate closes the internal hole and perform a process of switching to the standby mode, after a preset second elapse time.

In the non-contact safety relaying apparatus, the opening and closing unit may include: a cylindrical cover extending upward from an upper surface, surrounding an upper edge of the relaying hole, of the horizontal partition, and being closed at a top thereof and having an accommodation space formed to have an opening at a front side of the accommodation space, with the object being introduced through the opening; at least two partition wings being formed to extend radially from a rotation shaft extending downward from a center of an upper portion of the cylindrical cover, and thus to partition the accommodation space into a plurality of partition spaces including a partition space communicating with the relaying hole and a partition space not communication with the relaying hole, but communicating with the opening, by rotation of the partition wings; a motor driving the rotation shaft; a third road cell being mounted on a portion of the horizontal partition, with the portion thereof being exposed to the opening within the accommodation space in the cylindrical cover; a controller configured such that, when a load detection signal indicating safe arrival of the object is received from the third load cell, the controller drives rotation of the motor in such a manner that an interfering motion due to the rotation of the partition wings causes the object to drop into the relaying hole.

The non-contact safety relaying apparatus may further include a disinfecting solution spraying unit configured to spay a disinfecting solution into the accommodation space in which the third load cell is installed, wherein after the partition wings are rotated in such a manner that the object drops into the relaying hole, the controller may control the disinfecting solution spraying unit in such a manner that the disinfecting solution is sprayed into the accommodation space in which the third load cell is installed.

In the non-contact safety relaying apparatus, the opening and closing unit may include: an ascending and descending stable-landing plate configured to close the relaying hole in the horizontal partition from under the horizontal partition and to cause the object safely arriving through the relaying hole to descend vertically, while maintaining the same state as when the object arrives safely; and an ascending and descending drive unit configured to cause the ascending and descending stable-landing plate to ascend and descend vertically.

Advantageous Effects

The non-contact safety relaying apparatus for transferring an object according to the present invention provides the advantage of safely transferring an object designated to be transferred between different partition spaces while preventing spread of infection.

MODE FOR INVENTION

A non-contract safety relaying apparatus for transferring an object according to preferred embodiments of the present invention will be described in more detail below with reference to the accompanying drawings.

Figure 1:
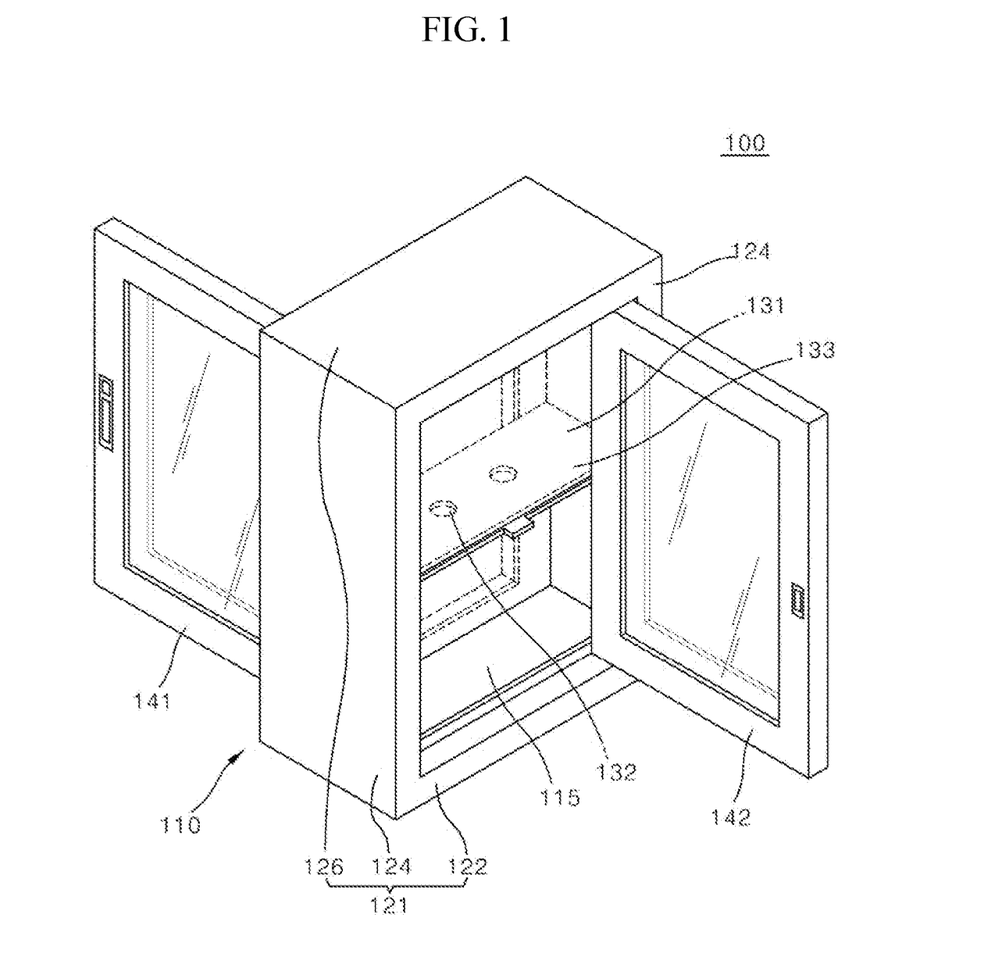
FIG. 1 is a perspective view illustrating a non-contract safety relaying apparatus for transferring an object according to a first embodiment of the present invention.
Figure 2:
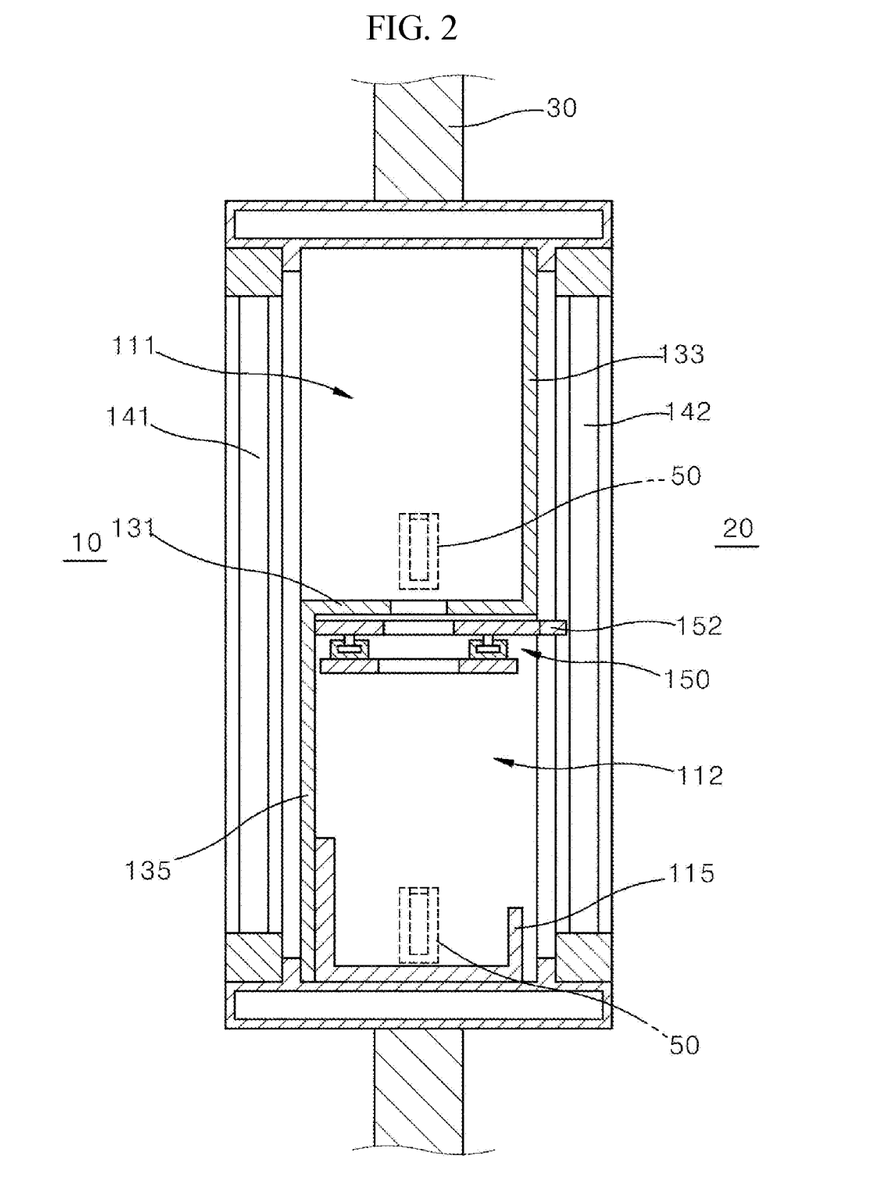
FIG. 2 is a cross-sectional view illustrating a state where the non-contact safety relaying apparatus for transferring an object in FIG. 1 is installed.
Figure 3:
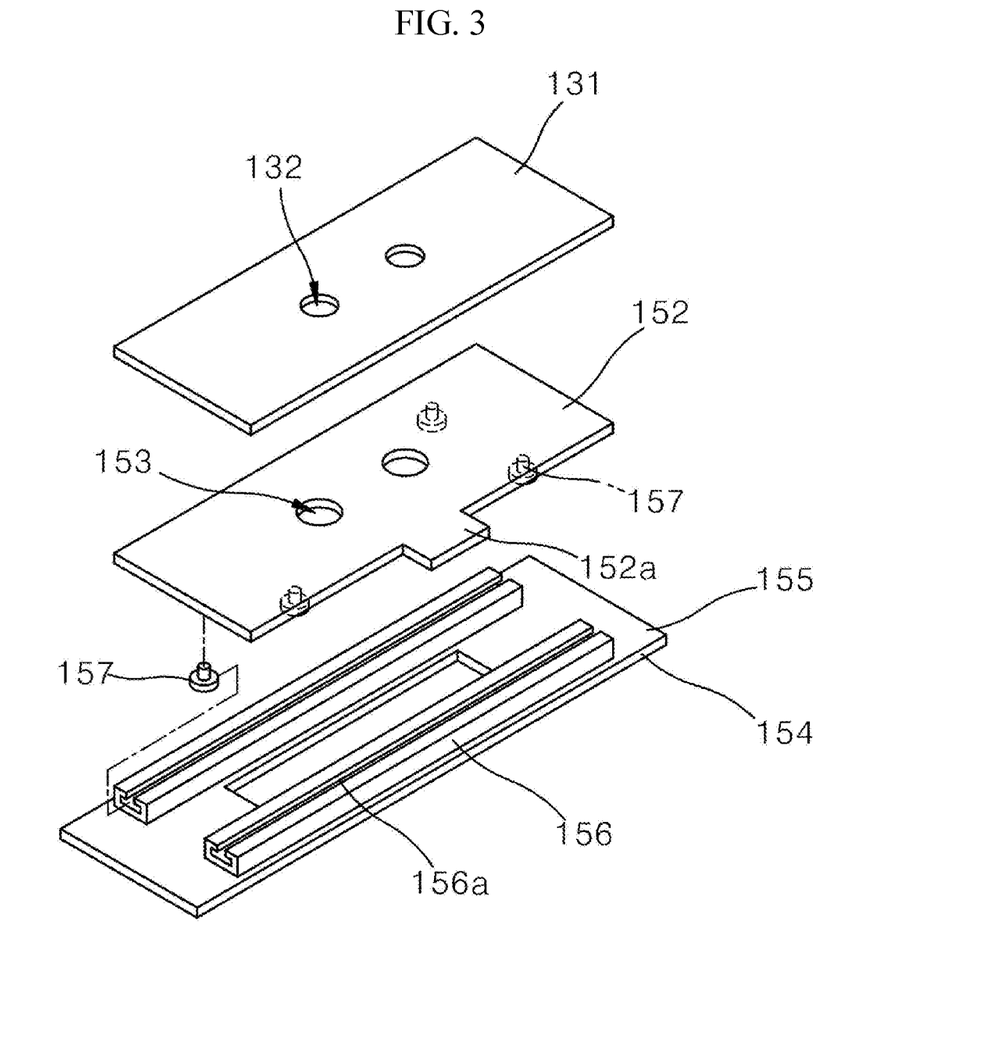
FIG. 3 is a broken-away perspective view illustrating an opening and closing unit opening and closing a relaying hole in a horizontal partition in FIG. 1.

FIG. 1 is a perspective view illustrating a non-contract safety relaying apparatus for transferring an object according to a first embodiment of the present invention. FIG. 2 is a cross-sectional view illustrating a state where the non-contract safety relaying apparatus for transferring an object in FIG. 1 is installed. FIG. 3 is an exploded view illustrating an opening and closing unit which opens and closes a relaying hole in a horizontal partition in FIG. 1.

With reference to FIGS. 1 to 3, the non-contact safety relaying apparatus 100 for transferring an object according to the present invention includes an apparatus body 110 and an opening and closing unit 150.

The apparatus body 110 is formed to have first and second relaying spaces 111 and 112. The first and second relaying spaces 111 and 112 are arranged between a first independent space 10 and a second independent space 20 that are separated independently of each other. The first and second relaying spaces 111 and 112 are positioned separately from each other to stably relay a specimen containing kit 50, which is an object to be transferred and is introduced from the first independent space 10, into the second independent space 20. Reference number 30 in FIG. 2 depicts a wall on which the apparatus body 110 is mounted in a buried manner and by which the first independent space 10 and the second independent space 20 are separated from each other. In addition, the first independent space 10 is a space in which the specimen is obtained, and the second independent space 20 is a space into which the specimen containing kit 50 is collected.

The apparatus body 110 has a structure including a main body 121, a horizontal partition 131, an upper partition 133, a lower partition 135, and first and second doors 141 and 142.

The main body 121 is formed to have an internal space through which the first independent space 10 and the second independent space 20 communicate with each other and is arranged in a direction that traverses the first independent space 10 and the second independent space 20.

The main body 121 includes a bottom plate 122, flank plates 124, and an upper plate 126. The bottom plate 122 forms a bottom surface. The flank plates 124 extends upward from both ends, respectively, of the bottom plate 122. The upper plate 126 connects upper ends of the flank plates 124 with each other.

The horizontal partition 131 extends horizontally at a height of the center of the main body 121, combines to each of the flank plates 124 which faces each other, and thus partitions the internal space into an upper space and a lower space. A plurality of relaying holes 132 is formed to be vertically pierced through the horizontal partition 131. Through the plurality of relaying holes 132, the upper space and the lower space communicate with each other. Unlike the illustrated example, of course, only one relaying hole 132 may be formed in the horizontal partition 131. The plurality of relaying holes 132 need to be formed to have a size suitable for providing a moving path of the specimen containing kit 50.

The upper partition 133 extends upward from one side of the horizontal partition 131, the side being exposed to the second independent space 20, and, along with the lower partition 135 described below, forms the first relaying space 111 which is exposed to the first independent space 10.

The lower partition 135 extends downward from a second side of the horizontal partition 131, the side being exposed to the first independent space 10, and, along with the upper partition 133, forms the second relaying space 112 which is exposed to the second independent space 20.

The first door 141 is combined with a side of the main side 121 using a hinge in such a manner as to open and close the first relaying space 111 to the first independent space 10. The first door 141 is formed to have a pane of transparent glass through which the first relaying space 111 can be viewed, and the main body 121 is formed to have a locking unit locking and unlocking the first door 141.

The second door 142 is combined with a second side of the main body 121 using a hinge in such a manner as to open and close the second relaying space 112 to the second independent space 20. The second door 142 is also formed to have a transparent pane of glass through which the second relaying space 112 can be viewed, and the main body 121 is also formed to have a locking unit locking and unlocking the second door 142.

Reference numeral 115 depicts a collection container installed on the bottom plate 122 under the horizontal partition 131 to accommodate the specimen containing kit 50 which drops from the first relaying space 111 into the second relaying space 112.

The opening and closing unit 150 is configured to open and close the relaying holes 132 in the horizontal partition 131.

The opening and closing unit 150 is arranged under the horizontal partition 131 and is configured to manually open and close the relaying holes 132 by a user's operation. The opening and closing unit 150 includes a slider 152, a guide portion 154, and a movable insertion piece 157.

Communicating holes 153 communicating with the relaying holes 132, respectively, are formed in the slider 152. The slider 152 is formed to have the shape of a plate, and thus a sliding movement thereof opens and closes the relaying holes 132. The slider 152 is arranged beneath the horizontal partition 131. A handler 152a protruding toward the second independent space 20 is formed on the slider 152.

The slider 152 is arranged in such a manner as to be moved in state of being in close contact with the horizontal partition 131. A sealing band is formed around an edge of the slider 152 in such a manner that an area in the vicinity of the relaying hole 132 in the horizontal partition 131 is sealed, and thus, the slider 152 can be kept in contact with the horizontal partition 131.

A support plate 155 and rails 156 are mounted on the guide portion 154. The support plate 155, positioned under the slider 152, is combined with the flank plates 124 of the apparatus body 110 in a manner that is supportable thereon. A holding groove 156a having an opening on top is formed in each of the rails 156. The rails 156 are mounted on an upper surface of the support plate 155.

The holding groove 156a formed in each of the rails 156 has a narrow upper portion and a wide lower portion.

The movable insertion piece 157 is combined with a bottom portion of the slider 152 and is moved in a secured state where a portion thereof is inserted into the holding groove 156a in the rail 156.

With this structure, the slider 152 is positioned to wait at an initial position for closing the relays hole 132 and, when the specimen containing kit 50 is placed safely in the relaying hole 132, is moved to a position where the communicating hole 153 in the slider 152 corresponds to the relaying hole 132. Then, after the specimen containing kit 50 is caused to drop through the communicating hole 153, the slider 152 is moved to return to the initial position.

Figure 4:
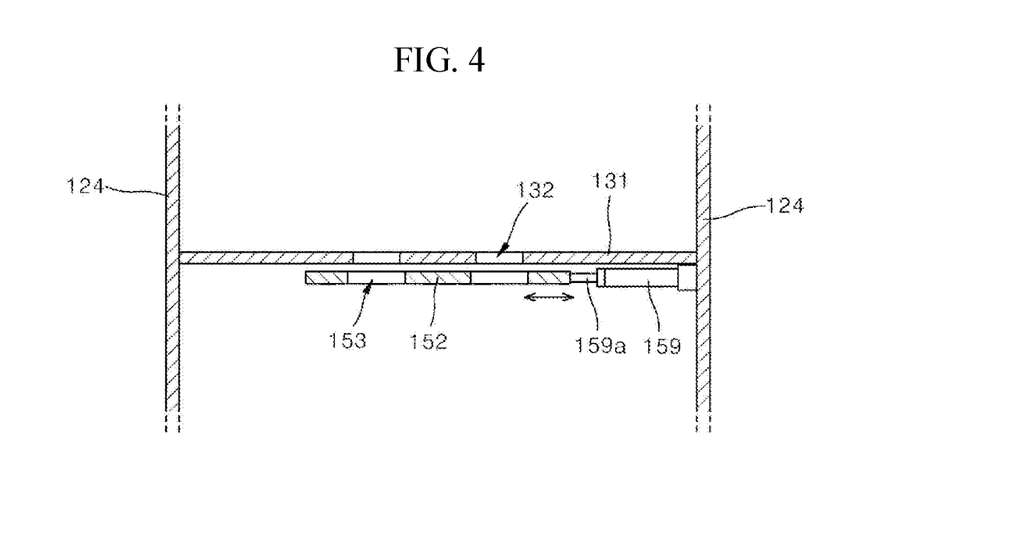
FIG. 4 is a cross-sectional view illustrating an opening and closing unit according to a second embodiment of the present invention.

Of course, a different structure may be employed as illustrated in FIG. 4. The slider 152 is combined with a rod 159a of a cylinder 159. As the rod 159a is moved backward and backward, the slide 152 is moved backward and forward. Thus, as described above, whether the relaying hole 132 is opened or closed depends on whether or not the communication hole 153 corresponds to the relaying hole 132.

Figure 8:
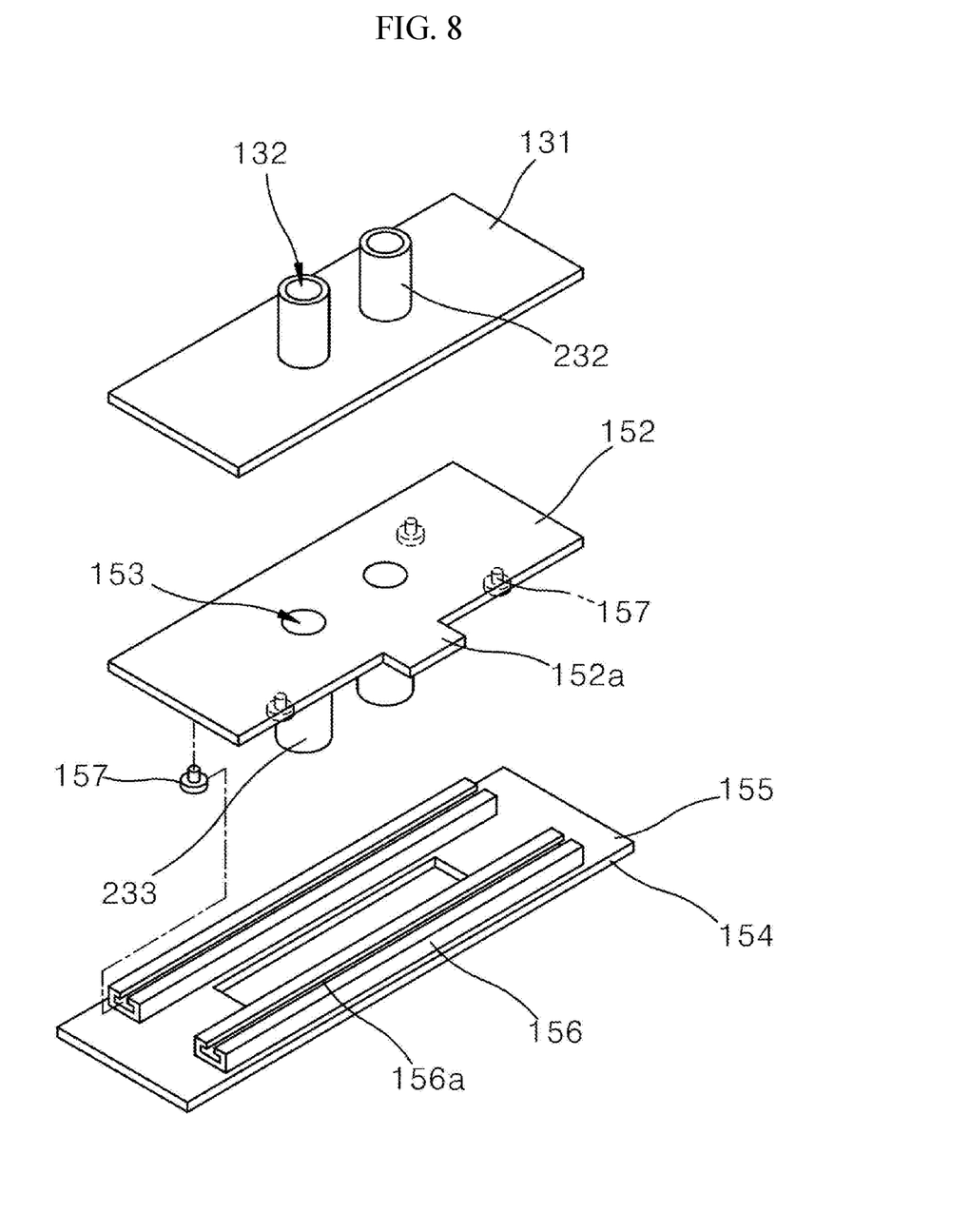
FIG. 8 is a broken-away perspective view illustrating an opening and closing unit according to a fifth embodiment of the present invention.

In addition, as illustrated in FIG. 8, of course, a structure further including an upper guide pipe 232 and a lower guide pipe 233 may be employed in order to limit introduction of external air while carrying the specimen containing kit 50 along a moving path. The upper guide pipe 232 extends upward from an upper surface, surrounding an upper edge of the relaying hole 132, of the horizontal partition 131 in such a manner that an internal space in the upper guide pipe 232 communicates with the relaying hole 132. The lower guide pipe 233 extends download from a lower surface, surrounding a lower edge of the communicating hole 153, of the slider 152 in such a manner that an internal space in the lower guide pipe 233 communicates with the communicating hole 153.

A double blocking structure may be employed in order to assure that the specimen containing kit 50 is moved more stably from the first relaying space 111 to the second relaying space 112 in such a manner as to prevent spread of infection. An example of such a structure is described with reference to FIG. 5. For simple drawing, a structure where one relaying hole 132 is formed in the horizontal partition 131 is illustrated in FIG. 5.

Figure 5:
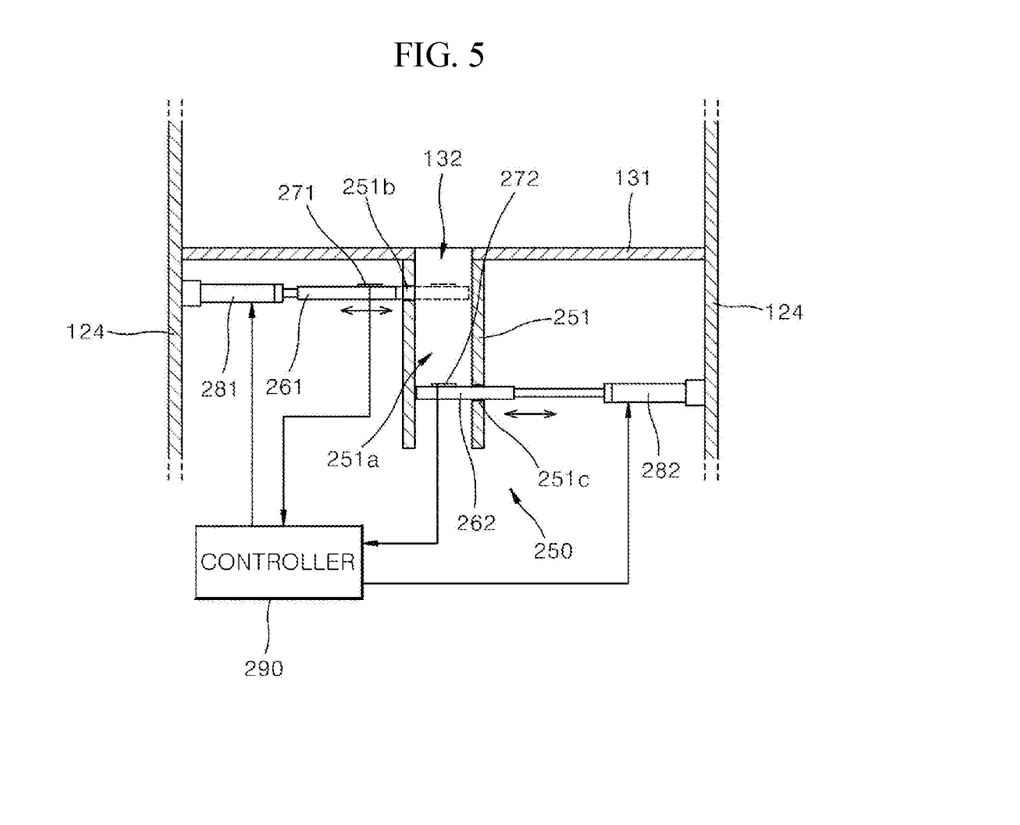
FIG. 5 is a cross-sectional view illustrating an opening and closing unit according to a third embodiment of the present invention.

With reference to FIG. 5, an opening and closing unit 250 includes an upright-positioned cylindrical pipe 251, an upper opening and closing plate 261, a lower opening and closing plate 262, a first load cell 271, a second load cell 272, a first actuator 281, a second actuator 282, and a controller 290.

In terms of structure, the upright-positioned cylindrical pipe 251 having an internal hole 251a pierced vertically therethrough extends downward from a bottom portion of the horizontal partition 131 in such a manner as to communicate with the relaying hole 132 in the horizontal partition 131. The upright-positioned cylindrical pipe 251 is configured to have a sufficiently longer length than the specimen containing kit 50. An upper inlet-outlet hole 251b and a lower inlet-outlet hole 251c are formed in the upright-positioned cylindrical pipe 251. The upper inlet-outlet hole 251b and lower inlet-outlet hole 251c pass horizontally through a wall of the upright-positioned cylindrical and communicate with the internal hole 251a, the upper inlet-outlet hole 251b and lower inlet-outlet hole 251c being a vertical distance away from each other. At this point, positions of the upper inlet-outlet hole 251b and the lower inlet-outlet hole 251c are determined in such a manner that the vertical distance therebetween is greater than a length of the specimen containing kit 50 to be transferred.

The upper opening and closing plate 261 is mounted into the upper inlet-outlet hole 251b in a manner that is movable backward and forward. Thus, the upper opening and closing plate 261 passes through the upper inlet-outlet hole 251b formed in the upright-positioned cylindrical pipe 251 and moves horizontally within the upright-positioned cylindrical pipe 251, thereby closing and opening the internal hole 251a.

The lower opening and closing plate 262 is mounted into the lower inlet-outlet hole 251c in a manner that is movable backward and forward. Thus, the lower opening and closing plate 262 passes through the lower inlet-outlet hole 251c formed at a distance below the upper inlet-outlet hole 251b and moves horizontally within the upright-positioned cylindrical pipe 251, thereby closing and opening the internal hole 251a.

The first load cell 271, mounted on the upper opening and closing plate 261, measures a weight of an object arriving safely thereon and provides the measured weight to the controller 290.

The second load cell 272, mounted in the lower opening and closing plate 262, measures a weight of an object arriving safely thereon and provides the measured weight to the controller 290.

The first actuator 281 moves the upper opening and closing plate 261 backward and forward through the upper inlet-outlet hole 251b, and thus opens or closes the internal hole 251a. An example is illustrated where a cylinder that moves a rod, combined with the upper opening and closing plate 261, backward and forward is provided.

The second actuator 282 moves the lower opening and closing plate 262 backward and forward through the lower inlet-outlet hole 251c, and thus opens or closes the internal hole 251a. An example is illustrated where a cylinder moves a rod, combined with the lower opening and closing plate 262, backward and forward is provided.

When signals detected by the first load cell 271 and the second load cell 272 both indicate a non-load state where an object does not arrive safely, the controller 290 determines that a standby mode is entered. In the standby mode, the controller 290 controls the first and second actuators 281 and 282 in such a manner that both the upper opening and closing plate 261 and the lower opening and closing plate 262 are loaded at positions, respectively, for closing the internal hole 251a.

In addition, when a load detection signal indicating safe arrival of that the specimen containing kit 50 is received from the first load cell 271 in the standby mode, after a preset first elapse time, the controller 290 controls the first actuator 281 in such a manner that the upper opening and closing plate 261 is moved to a position for opening the internal hole 251a. Then, when a load detection signal indicating safe arrival of the dropping specimen containing kit 50 is received from the second load cell 272, the controller 290 controls the first actuator 281 in such a manner that the upper opening and closing plate 261 is moved to a position for closing the internal hole 251a, and controls the second actuator 282 in such a manner that the lower opening and closing plate 262 is moved to a position for opening the internal hole 251a and thus the specimen containing kit 50 drops. After a preset second elapse time, the controller 290 controls the second actuator 282 in such a manner that the lower opening and closing plate 262 closes the internal hole 251a, and performs a process of switching to the standby mode.

With this method, the process of keeping the specimen containing kit 50 in an enclosed state within the upright-positioned cylindrical pipe 251 is further performed when the specimen containing kit 50 is transferred between the first independent space 10 in which a negative pressure is maintained and the second independent space 20 in which a positive pressure is maintained. Thus, the assurance of the stability in transfer while transferring the specimen containing kit 50 can be increased.

Unlike the illustrated example, an opening and closing unit relaying the specimen containing kit 50 in a manner that rotates the specimen containing kit 50 may be provided. An example of thereof is described with reference to FIGS. 6 and 7.

Figure 6:
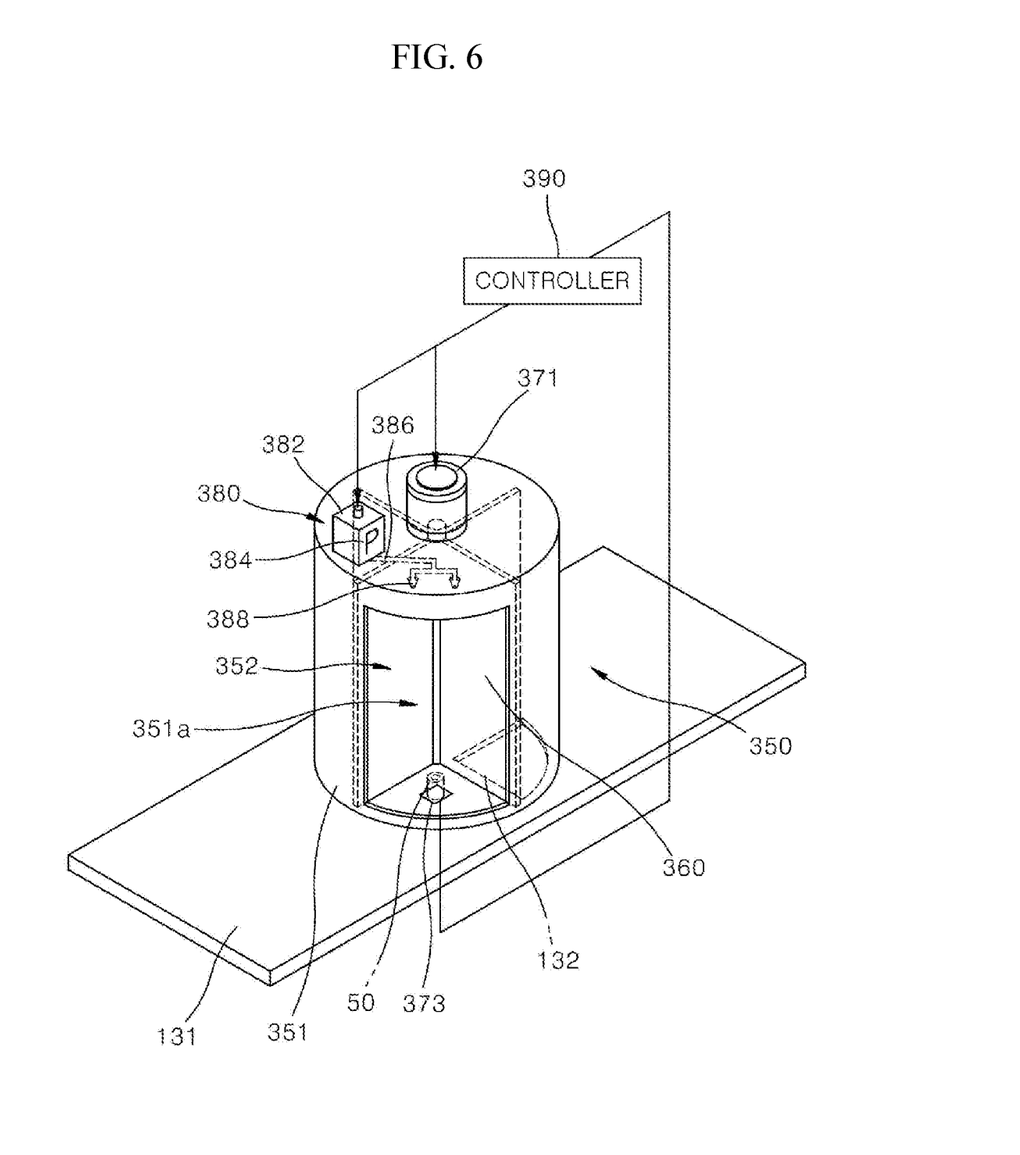
FIG. 6 is a view illustrating an opening and closing unit according to a fourth embodiment of the present invention.
Figure 7:
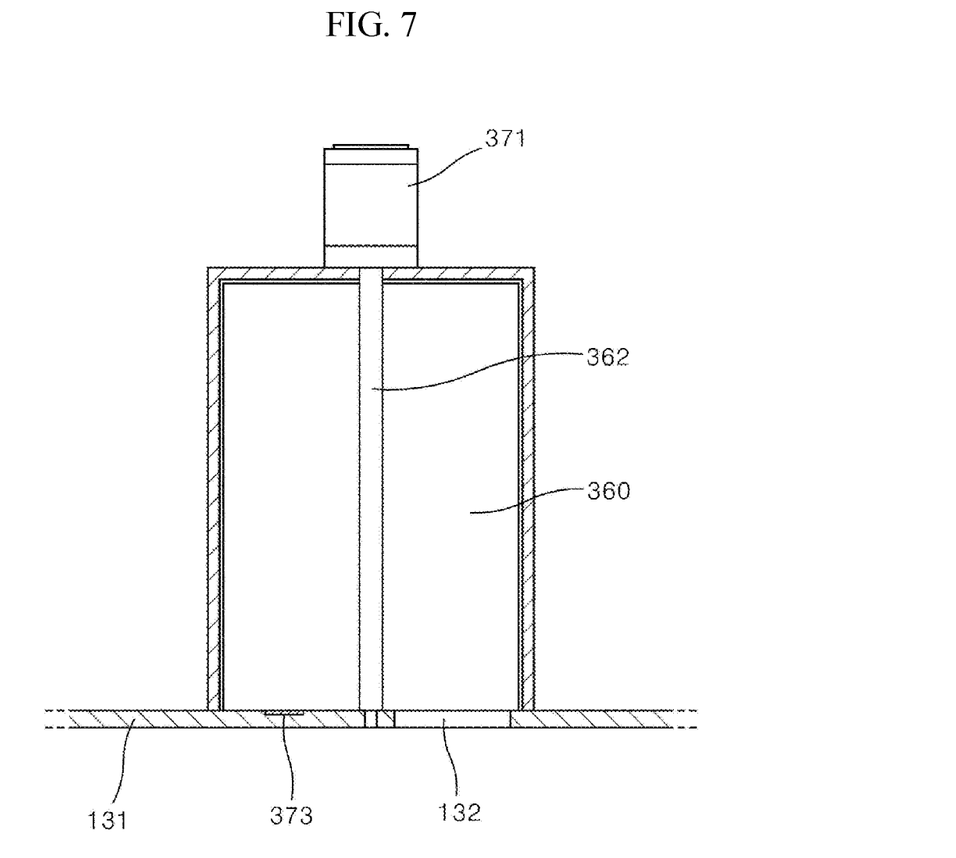
FIG. 7 is a longitudinal cross-sectional view illustrating a cylindrical cover in FIG. 1.

With reference to FIGS. 6 and 7, an opening and closing unit 350 includes a cylindrical cover 351, partition wings 360, a motor 371, a third load cell 373, a disinfecting solution spraying unit 380, and a controller 390.

In terms of structure, the cylindrical cover 351 is closed at the top and has an accommodation space 351a formed to have an opening 352 at the front side. The cylindrical cover 351 extends upward from an upper surface, surrounding an upper edge of the relaying hole 132, of the horizontal partition 131. The specimen containing kit 50 is introduced through the opening 352.

The cylindrical cover 351 is formed to have the shape of a cylinder, and a lower portion thereof is jointed to the horizontal partition 131.

The partition wings 360 extends in the shape of a plate radially from a rotation shaft 362 extending downward from the center of an upper portion of the accommodation space 351a in the cylindrical cover 351. Thus, the partition wings 360 partition the accommodation space 351a into a plurality of partition spaces including four partition spaces, along a circumferential direction. The four partition spaces are positioned at equal distances from each other, making an angle of 90 degrees therebetween along the circumferential direction. With rotation of the partition wings 360, two partition spaces communicate with the relaying hole 132 in the horizontal partition 131, and the other two partitions do not communicate with the relaying hole 132, but communicate with the opening 352.

In this case, by the four partition wings 360, the four partition spaces are formed in the accommodation space 351a in the cylindrical cover 351. Unlike the illustrated example, of course, two or three partition wings 360 may be provided.

The motor 371 is mounted stably on an upper surface of the cylindrical cover 351 and drive rotation of the rotation shaft 362 connected to the partition wings 360 under the control of the controller 390.

The third load cell 373 is mounted on a portion of the horizontal partition 131, which is exposed to the opening 352 within the accommodation space 351a in the cylindrical cover 351. The third load cell 373 provides to the controller 390 the load detection signal corresponding to whether or not the specimen containing kit 50 arrives safely.

Under the control of the controller 390, the disinfecting solution spraying unit 380 sprays a disinfecting solution into the accommodation space 351a in which the third load cell 373 is installed.

The disinfecting solution spraying unit 380 includes a storage tank 382, a pump (p) 384, and a supply pipe 386. A disinfecting solution is stored in the storage tank 382. The pump 384 pumps the disinfecting solution stored in the storage tank 382. The supply pipe 386 extends from the storage tank 382 to a nozzle 388 that is mounted in a manner that is exposed into the accommodation space 351a. The nozzle 388 is mounted in such a manner as not to interfere with rotation of the partition wings 360. A valve (not illustrated) that opens and closes the supply pipe 386 under the control of the controller 390 is installed.

When the load detection signal corresponding to safe arrival of the specimen containing kit 50 is received from the third load cell 373, the controller 390 drives rotation of the motor 371 in such a manner that an interfering motion due to the rotation of the partition wings 360 causes the specimen containing kit 50 to drop into the relaying hole 132. At this point, in a case where a structure where the partition wings 360 are arranged in such a manner that the rotation of the partition wings 360 by an angle of 90 degrees causes the specimen containing kit 50 to drop through the relaying hole 132 is employed, the controller 390 can be configured to rotate the partition wings 360 by an angle of 90 degrees or 360 degrees.

In addition, the controller 390 controls the motor 371 and thus rotates the partition wings 360 in such a manner that the specimen containing kit 50 drops into the relaying hole 132. Thereafter, the controller 390 controls the disinfecting solution spraying unit 380 for a preset disinfecting time in such a manner that the disinfecting solution spraying unit 380 is driven to spray the disinfecting solution into the accommodation space 351a in which the third road cell 373 is installed. In this case, a relaying space for transferring the specimen containing kit 50 is disinfected whenever the specimen containing kit 50 is transferred, and thus the assurance of protection against infection can be further increased.

The non-contact safety relaying apparatus 100 for transferring an object is configured in such a manner that the specimen containing kit 50 is obtained in the first independent space 10 and that the obtained specimen containing kit 50 is transferred into the second independent space 20 for collecting. In an environment where the first independent space 10 maintains a lower pressure, that is, a negative pressure, than the second independent space 20, the first door 141 is opened, and thus the specimen containing kit 50 obtained in the first independent space 10 is caused to arrive safely in a transfer position within the first relaying space 111. Thereafter, the first door 141 is closed. Next, in a case where the non-contact safety relaying apparatus 100 is operated manually, the second door 142 is opened, and the above-described opening and closing unit 150 is operated in the second relaying space 112 in such a manner that the specimen containing kit 50 drops through the relaying hole 132. Thereafter, the relaying hole 132 is closed and the collected specimen containing kit 50 is moved into the second independent space 20. Then, the second door 142 is closed. Otherwise, in a case where the non-contact safety relaying apparatus 100 is configured in such a manner that the specimen containing kit 50 automatically drops through the relaying hole 132 under the control of the controller 290 or 390, at a specified time, the second door 142 is opened and the specimen containing kit 50 collected in the collection container 115 is taken out.

The non-contact safety relaying apparatus 100 may be configured in such a manner that the specimen containing kit 50 drops, maintaining the same state as when the object arrives safely, instead of in free fall. An example thereof is described with reference to FIG. 9. A constituent element having the same function as that described above is given the same reference numeral as that described above.

Figure 9:
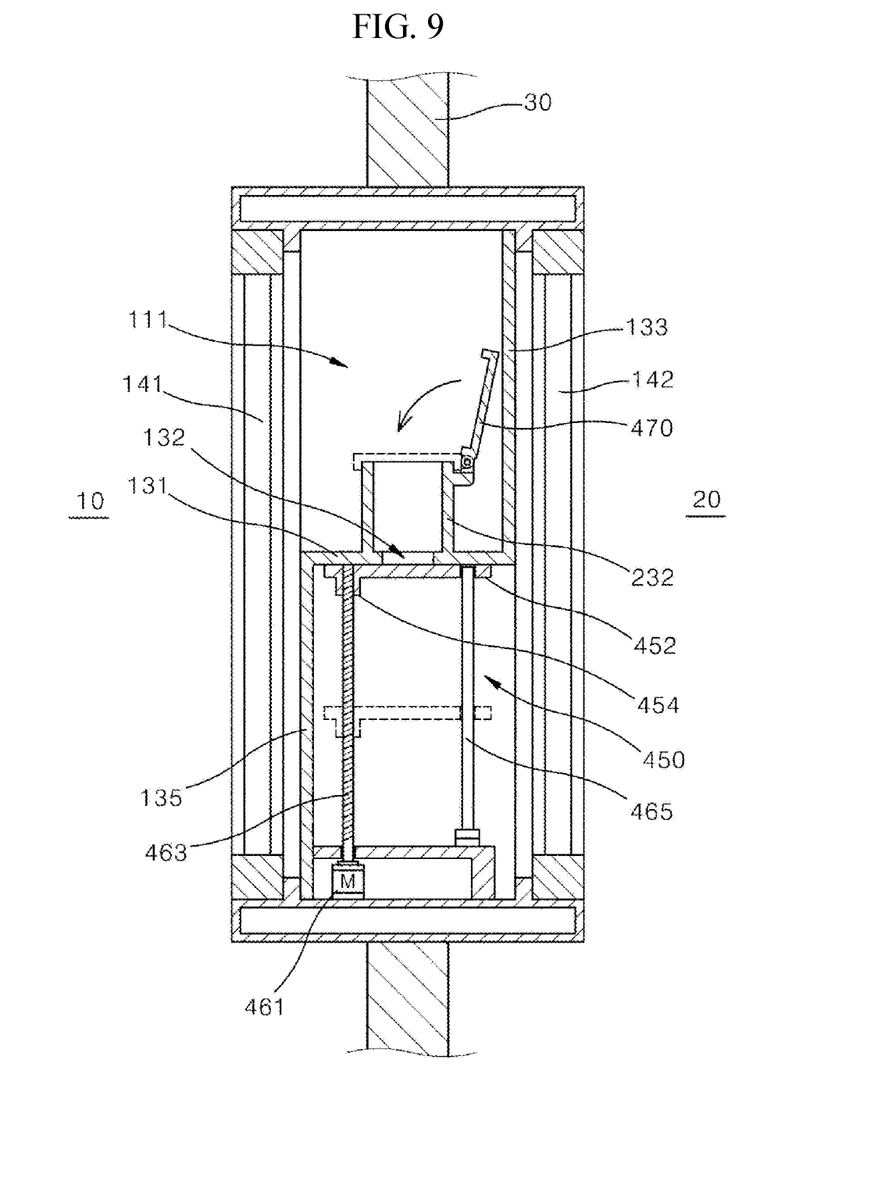
FIG. 9 is a cross-sectional view illustrating an opening and closing unit according to a sixth embodiment of the present invention.

With reference to FIG. 9, an opening and closing unit 450 includes an ascending and descending stable-landing plate 452 and an ascending and descending drive unit.

The ascending and descending stable-landing plate 452 is formed to have the shape of a plate in such a manner that an object designated to be transferred safely arriving on the ascending and descending stable-landing plate through the relaying hole 132 descends vertically, maintaining the same state as when the object arrives safely. The ascending and descending stable-landing plate 452 closes the relaying hole 132 in the horizontal partition 131 from under the horizontal partition 131. A sealing pad may be attached to a portion, brought into close contact with the horizontal partition 131 in the vicinity of the relaying hole 132, of the ascending and descending stable-landing plate 452 in such a manner that the ascending and descending stable-landing plate 452 is brought into close contact with a bottom surface of the horizontal partition 131, in a state of being sealed.

A nut 454 is formed to be integrated with the ascending and descending stable-landing plate 452. A screw 463 described below is screwed into the nut 454. In this manner, the screw 463 passes through the nut 454.

The ascending and descending drive unit is configured to include a motor 461, the screw 463, and a vertical guide bar 465. The ascending and descending drive unit causes the ascending and descending stable-landing plate 452 to ascend and descend vertically.

The screw 463 passes through the nut 454 of the ascending and descending stable-landing plate 452 and then extend vertically. A first end of the screw 463 is combined with a bottom portion of the horizontal partition 131 in a freely rotatable manner, and a second end thereof is combined with a rotation shaft of the motor 461.

The vertical guide bar 465 is installed to pass through the ascending and descending stable-landing plate 452 from a bottom portion of the horizontal partition 131 and then extend vertically in such a manner that, when the screw 463 is rotated clockwise or counterclockwise, the ascending and descending stable-landing plate 452 ascends or descends without any rotation.

A cover 470 that can close an internal hole in the upper guide pipe 232 from above is rotatably provided on an upper portion of the upper guide pipe 232.

In addition, through an operation unit that is not illustrated, the motor 461 is instructed to rotate clockwise or counterclockwise in a manner that corresponds to the ascending or descending of the ascending and descending stable-landing plate 452. Then, the rotation of the motor 461 causes the ascending descending stable-landing plate 452 to ascend or descend. Therefore, after the object designated to be transferred arrives safely on the ascending and descending stable-landing plate 452, the cover 470 and the motor 461 is operated to cause the ascending and descending stable-landing plate 452 to descend. Thus, the object designated to be transferred is caused to descend stably. When the object designated to be transferred is completely transferred, the motor 461 is controlled in such a manner that the ascending and descending stable-landing plate 452 ascends to an initial position thereof.

In addition, of course, a structure may be employed where a load cell is mounted on the ascending and descending stable-landing plate 452 and where the ascending and descending stable-landing plate 452 automatically ascends and descend according to whether or not a load on the load cell is detected.

In addition, of course, a structure may be employed where the cover 470 is opened and closed in a manner that corresponds to whether the ascending and descending stable-landing plate 452 ascends or descends. With this structure, when the ascending and descending stable-landing plate 452 ascends, control is performed in such a manner that the cover 470 is automatically closed. Then, when the ascending and descending stable-landing plate 452 ascends and returns to the initial position thereof, controls is performed in such a manner that the cover 470 is opened.

In addition, although not illustrated, a structure may be employed where a microphone and a speaker is mounted on each of the first and second doors 141 and 142 and where wiring is provided in such a manner that voice that is input from one side can be output to the other side. In this case, when an object is going to be transferred, the microphone can be turned on and voice can be transferred to the other side through the speaker, and thus the object can be transferred more efficiently.

The specimen containing kit 50 is described above as the object designated to be transferred. In addition to the specimen containing kit 50, examples thereof include various objects such as eatables and drinkables.

The above-described non-contact safety relaying apparatus for transferring an object provides the advantage of safely transferring the object designated to be transferred between different partition spaces while preventing infection.

DESCRIPTION OF THE REFERENCE NUMERALS IN THE DRAWINGS

110: Apparatus body 121: Main body
131: Horizontal partition 141: First door
142: Second door 150, 250, 350: Opening and closing unit

The invention claimed is:

1. A non-contact safety relaying apparatus for transferring an object, which is arranged between a first independent space and a second independent space separated independently of each other and is configured to stably relay the object introduced from the first independent space into the second independent space in a non-contact manner, the apparatus comprising:
an apparatus body, wherein said apparatus body comprises:
a main body being formed to have an internal space through which the first independent space and the second independent space communicate with each other and being arranged in a direction that traverses the first independent space and the second independent space,
a horizontal partition extending horizontally at a height of a center of the main body, with at least one relaying hole being formed to be pierced through the horizontal partition,
an upper partition extending upward from a first side of the horizontal partition and forming a first relaying space exposed to the first independent space,
a lower partition extending downward from a second side which is the opposite side of the horizontal partition and forming a second relaying space exposed to the second independent space,
a first door mounted on the main body in such a manner as to open and close the first relaying space, and
a second door mounted on the main body in such a manner as to open and close the second relaying space, and
an opening and closing unit configured to open and close the relaying hole in the horizontal partition.

2. The non-contact safety relaying apparatus of claim 1, wherein the opening and closing unit comprises:
a slider being arranged beneath the horizontal partition with a communicating hole being formed in the slider to communicate with the relaying hole, and being configured to open and close the relaying hole by a sliding movement thereof,
a guide portion being positioned under the slider and being combined with the apparatus body in a manner that is supportable on the apparatus body, with a rail being formed on an upper portion of the guide portion; and
a movable insertion piece being combined with a bottom portion of the slider and being moved in a secured state along the rail.

3. The non-contact safety relaying apparatus of claim 1, wherein the opening and closing unit comprises:
an upright-positioned cylindrical pipe having an internal hole vertically pierced therethrough and extending downward from a bottom portion of the horizontal partition in such a manner as to communicate with the relaying hole in the horizontal partition;
an upper opening and closing plate being mounted into an upper inlet-outlet hole in a manner that is movable backward and forward, in such a manner as to pass through the upper inlet-outlet hole formed in the upright-positioned cylindrical pipe and to move horizontally within the upright-positioned cylindrical pipe, thereby closing and opening the internal hole;
a lower opening and closing plate being mounted into a lower inlet-outlet hole in a manner that is movable backward and forward, in such a manner as to pass through the lower inlet-outlet hole formed at a distance below the upper inlet-outlet hole and to move horizontally within the upright-positioned cylindrical pipe, thereby closing and opening the internal hole;
a first load cell mounted on the upper opening and closing plate;
a second load cell mounted on the lower opening and closing plate;
a first actuator to move the upper opening and closing plate backward and forward;
a second actuator to move the lower opening and closing plate backward and forward; and
a controller configured to determine that a standby mode is entered when signals detected by the first load cell and the second load cell indicate a non-load state, control in the standby mode the first and second actuators in such a manner that both the upper opening and closing plate and the lower opening and closing plate are loaded at positions for closing the internal hole, control the first actuator in such a manner that the upper opening and closing plate is moved to a position for opening the internal hole, after a preset first elapse time, when a load detection signal indicating safe arrival of the object is received from the first load cell in the standby mode, control the first actuator in such a manner that the upper opening and closing plate is moved to the position for closing the internal hole and control the second actuator in such a manner that the lower opening and closing plate is moved to a position for opening the internal hole and thus the object drops, when a load detection signal indicating safe arrival of the dropping object is received from the second load cell, and control the second actuator in such a manner that the lower opening and closing plate closes the internal hole and perform a process of switching to the standby mode, after a preset second elapse time.

4. The non-contact safety relaying apparatus of claim 1, wherein the opening and closing unit comprises:

a cylindrical cover extending upward from an upper surface, surrounding an upper edge of the relaying hole, of the horizontal partition, and being closed at the top thereof and having an accommodation space formed to have an opening at a front side of the accommodation space, with the object being introduced through the opening;

at least two partition wings being formed to extend radially from a rotation shaft extending downward from a center of an upper portion of the cylindrical cover, and thus to partition the accommodation space into a plurality of partition spaces including a partition space communicating with the relaying hole and a partition space not communicating with the relaying hole, but communicating with the opening, by rotation of the partition wings;

a motor driving the rotation shaft;

a third road cell being mounted on a portion of the horizontal partition, said portion of the horizontal partition being exposed to the opening within the accommodation space in the cylindrical cover;

a controller configured such that, when a load detection signal indicating safe arrival of the object is received from the third load cell, the controller drives rotation of the motor in such a manner that an interfering motion due to the rotation of the partition wings causes the object to drop into the relaying hole.

5. The non-contact safety relaying apparatus of claim 4, further comprising:

a disinfecting solution spraying unit configured to spray a disinfecting solution into the accommodation space in which the third load cell is installed, wherein after the partition wings are rotated in such a manner that the object drops into the relaying hole, the controller controls the disinfecting solution spraying unit in such a manner that the disinfecting solution is sprayed into the accommodation space in which the third load cell is installed.

6. The non-contact safety relaying apparatus of claim 1, wherein the opening and closing unit comprises:

an ascending and descending stable-landing plate configured to close the relaying hole in the horizontal partition from under the horizontal partition and to cause the object safely arriving through the relaying hole to descend vertically, while maintaining the same state as when the object arrives safely; and an ascending and descending drive unit configured to cause the ascending and descending stable-landing plate to ascend and descending vertically.

* * * * *